United States Patent [19]
Knauer

[11] Patent Number: 6,105,715
[45] Date of Patent: Aug. 22, 2000

[54] MULTI-COLOR VARIABLY ATTENUATING EARPLUG

[75] Inventor: Richard E. Knauer, Indianapolis, Ind.

[73] Assignee: Aearo Company, Cambridge, Mass.

[21] Appl. No.: 09/434,602

[22] Filed: Nov. 5, 1999

[51] Int. Cl.[7] .............................. A61B 7/02; A61F 11/00
[52] U.S. Cl. ............................................ 181/135; 128/864
[58] Field of Search .................................... 181/130, 135; 128/864, 865, 867

[56] References Cited

U.S. PATENT DOCUMENTS

| | | |
|---|---|---|
| Re. 29,487 | 12/1977 | Gardner, Jr. . |
| 4,158,087 | 6/1979 | Wood . |
| 5,203,352 | 4/1993 | Gardner, Jr. . |
| 5,573,015 | 11/1996 | Williams ................................ 128/864 |
| 5,792,998 | 8/1998 | Gardner, Jr. . |
| 5,811,742 | 9/1998 | Leight . |

*Primary Examiner*—Khanh Dang
*Attorney, Agent, or Firm*—Cantor Colburn LLP

[57] ABSTRACT

The present invention provides an earplug having a plurality of visual zones. In one embodiment, the earplug includes a first visual zone, a second visual zone, and a third visual zone. The first, second, and third visual zones each comprise continuous longitudinal color bands each of which extends completely around the circumference of the earplug. In one embodiment, at least the second visual zone intermediate the first and third visual zones is formed of a color which is distinctly different from the colors of the other visual zones. In another embodiment, the first, second, and third visual zones each have one color which is distinctly different than the other colors. Accordingly, the first, second, and third visual zones comprise visual zones which permit an observer or the wearer to immediately ascertain the depth of insertion of the earplug by simply viewing the earplug. In one aspect, this permits a safety officer or other individual, including the wearer, to easily determine whether the wearer is complying with existing safety rules and regulations. In another aspect, this permits the wearer to determine whether a proper fit exists between the earplug and the ear canal because each of the visual zones indicates the degree of insertion into the ear canal.

20 Claims, 2 Drawing Sheets

MULTI-COLOR VARIABLY ATTENUATING EARPLUG

BACKGROUND OF THE INVENTION

1. Field of the Invention

This invention relates generally to acoustic hearing protective devices and, more particularly, to an earplug having a plurality of visual zones which provide a method of indicating the depth of insertion of the earplug and the level of sound attenuation.

2. Brief Discussion of the Prior Art

Environmental sounds are typically comprised of a mixture of various sound wave frequencies having varying intensities. It is well documented that repeated or prolonged exposure to sounds of sufficiently high sound pressure level will cause temporary or permanent hearing loss. For example, exposure to sound waves of some frequencies and of varying intensities under prolonged exposure can damage the auditory organ and cause serious hearing problems, including deafness. Injurious noises such as those caused by explosions or bursts are often comprised of a mixture of sound wave frequencies of varying intensity. These disturbing frequencies are in both the high and low frequency bands and have an intensity sufficient to cause hearing problems. Individuals who are frequently exposed to sound having such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise. Sound attenuation devices are known which specifically address this problem. These include conventional earplugs, earmuffs, and the like which function to reduce the negative effects of exposure to dangerous frequencies by limiting the entry of all sound waves into the auditory organ.

One of the associated disadvantages of earplug use is that people generally do not like to place objects into their ears and wear them for periods of time. Also, because by nature, the earplugs are designed to attenuate noise, some users do not properly insert the earplugs into their ears in an effort to be able to more easily communicate with and hear other individuals surrounding the wearer, e.g., co-workers. In addition, many work environments are such that the use of hearing protection is required under corporate or other policies for safety reasons and in this type of work environment, some individuals only partially insert the earplug device into the their ears. To the casual observer, it would appear that these individuals are in compliance with the existing safety rules when in fact the earplugs are not properly inserted and consequently, the advantages offered by the hearing protective device, i.e., earplugs, are not realized and the wearer is exposed to greater levels of noise and greater risks. Even a trained individual, such as a supervisor or other hearing conservationist, may mistakenly believe that the individual is complying with the existing rules based solely on the visual observance of earplugs in the wearer's ears. Unless, the trained individual closely observes the manner in which the earplugs are inserted into the wearer's ears, it is difficult to judge whether any individual is in full compliance with existing safety rules.

Accordingly, it has been found to be very difficult to enforce the use of hearing protection without having spot checks where the degree of insertion of the earplugs into the wearer's ears is observed. When an individual is subjected to a spot check, the individual must discontinue working and thus productivity is lost due to the spot check. As the number of spot checks and the number of persons subjected to them increases, productivity will continue to decrease resulting in lower profitability and increasing production times. As a result, there is a need for a method and hearing protective device which permits the supervisor or another individual to more easily determine whether the wearer is complying with rules, regulations, and the like by wearing the dual hearing protective device.

SUMMARY OF THE INVENTION

The above-discussed and other drawbacks and deficiencies of the prior art are overcome or alleviated by the earplug of the present invention. The earplug broadly comprises a resilient polymeric foam body. In one exemplary embodiment, the earplug has a plurality of visual zones provided therein, wherein at least an intermediate visual zone is visually different from the remaining visual zones so as to demarcate the earplug into the plurality of visual zones. Preferably, the earplug includes at least three visual zones formed therein. In one exemplary embodiment, the earplug has first and second visual zones at first and second ends, respectively, and an intermediate visual zone, wherein the first and second visual zones have a first color and the intermediate zone has a second color. For example, the first and second visual zones have a yellow color and the intermediate zone has a red color.

In another exemplary embodiment, the earplug includes a first visual zone, a second visual zone, and a third visual zone. In this embodiment, the first, second, and third visual zones comprise colored visual zones. In the exemplary embodiment, the first, second, and third visual zones each comprise continuous longitudinal color bands each of which preferably extends completely around the circumference of the earplug. The first, second, and third visual zones each have a color which is distinctly different than the other colors. In one exemplary embodiment, the first visual zone has a red color, the second visual zone has a yellow color, and the third visual zone has a green color. The first visual zone comprises the insertion end of the earplug, while the second zone comprises an intermediate portion of the earplug and the third visual zone comprises the second end of the earplug. Accordingly, the first, second, and third visual zones comprise visual zones which permit an observer or the wearer to immediately ascertain the depth of insertion of the earplug by simply viewing which visual zone(s) of the earplug is visible. This permits a safety officer or other individual, including the wearer, to easily determine whether the wearer is complying with existing safety rules and regulations.

For example, if the wearer inserts the earplug into his/her ears and any amount of the red color of the first visual zone is visually apparent, this indicates a poor fit between the earplug and the ear canal. Consequently, the earplug should be removed and re-fitted. This also indicates that the wearer is only experiencing a low level of sound attenuation because the earplug is not properly inserted into the ear. If the earplug is inserted so that the red color of the first visual zone is not apparent but a portion of the yellow color of the second visual zone is visually apparent, this indicates a moderate fit of the earplug. In other words, the wearer is obtaining some sound attenuation but is not obtaining maximum sound attenuation. If only a portion of the green color of the third visual zone is visually apparent, then the fit between the earplug and the ear canal is good and optimum attenuation is obtained.

Furthermore, the use of visual zones are also used to aid the wearer in obtaining a better fit for the earplug. For example, the wearer may view the depth of insertion of the earplug into the wearer's ear by using appropriate devices, e.g., a mirror. By observing which visual zones are visible, the wearer can immediately ascertain the degree of the fit and the corresponding level of sound attenuation being offered by the earplug. Adjustments may then be made, if needed, so that the earplug is properly being worn.

Thus, the visual zones of the present invention serve as visual markings for indicating various depths of insertion into the ear canal and various levels of sound attenuation. Furthermore, the earplug of the present invention advantageously provides a convenient method of determining whether the wearer is complying with existing safety regulations and rules and the like.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DETAILED DESCRIPTION OF THE PREFERRED EMBODIMENT

Figure 1:
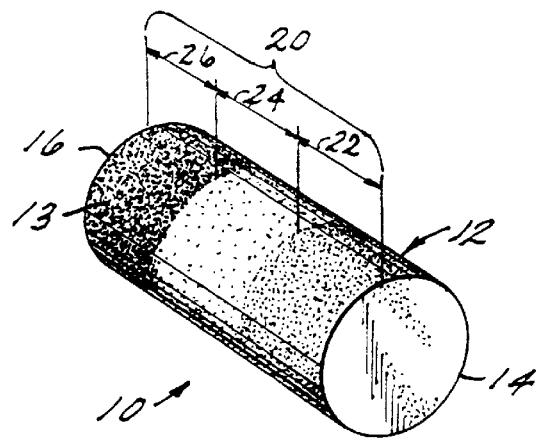
FIG. 1 is a perspective view of an earplug according to a first embodiment of the present invention.

Referring now to FIG. 1 in which an exemplary earplug construction according to a first embodiment of the present invention is illustrated and generally indicated at 10. The earplug 10 broadly comprises a resilient polymeric foam body 12. The earplug 10 is generally cylindrical in shape and has an insertion end 14 and an opposing second end 16. The diameter of the earplug 10 is somewhat greater than that of the average adult human ear canal. In the first exemplary embodiment, a plurality of visual zones 20 are provided in the earplug 10. As best shown in FIG. 1, the earplug 10 includes a first visual zone 22, a second visual zone 24, and a third visual zone 26. In this embodiment, the first, second, and third visual zones 22, 24, 26 comprise colored visual zones. As shown, the first, second, and third visual zones 22, 24, 26 each comprise a longitudinal color band. According to the first embodiment, at least the second zone 24 is formed of a color which is distinctly different from the first and third visual zones 22, 26. In other words, the first and third visual zones 22, 26 may have the same color; however, the second visual zone 24 which is intermediate the first and third visual zones 22, 26 has a color distinctly different from the other visual zones 22, 26. For example, in one preferred embodiment, the first and third visual zones 22, 26 have a yellow color and the second visual zone 24 has a red color. In the first embodiment, the visual zones 22, 24, 26 comprise continuous color bands each of which extends completely around the circumference of the earplug 10.

The first visual zone 22 comprises the insertion end 14 of the earplug 10. The second zone 24 comprises an intermediate portion of the earplug 10 and the third visual zone 26 comprises the second end 16 of the earplug 10. Accordingly, the first, second, and third visual zones 22, 24, 26 comprise visual zones which permit a safety officer or other individual to ascertain whether the wearer is complying with existing safety rules and regulations. For example, if the wearer inserts the earplug 10 into his/her ears and any amount of the yellow color of the first visual zone 22 is visually apparent to an observer, this indicates that a poor fit between the earplug 10 and the ear canal. Consequently, the earplug 10 should be removed and re-fitted. This also indicates that the wearer is only experiencing a low level of sound attenuation because the earplug 10 is not properly inserted into the ear.

If the earplug 10 is inserted so that the yellow color of the first visual zone 22 is not apparent but a portion of the red color of the second visual zone 24 is visually apparent, this indicates a moderate fit of the earplug 10. In other words, the wearer is obtaining some sound attenuation but is not obtaining maximum sound attenuation. If only a portion of the yellow color of the third visual zone 26 is visually apparent, then the fit between the earplug 10 and the ear canal is good and optimum attenuation is obtained. It being understood that the invention is not limited to the use of yellow and red colors and a number of color combinations may be used so long as the colors mark or indicate a plurality of visual zones 20 which permit the observer to readily and easily know the type of fit between the earplug 10 and the ear canal and accordingly, the level of sound attenuation being provided by earplug 10. Furthermore, the use of visual zones 22, 24, 26 helps to aid the wearer in obtaining a better fit for the earplug 10. For example instead of the safety officer being the observer, the wearer may view the depth of insertion of the earplug 10 into the wearer's ear by using appropriate devices, e.g., a mirror. By observing which of visual zones 22, 24, 26 are visible, the wearer can immediately ascertain the degree of the fit and the corresponding level of sound attenuation being offered by the earplug 10. Adjustments may then be made, if needed, so that the earplug 10 is properly being worn.

Figure 2:
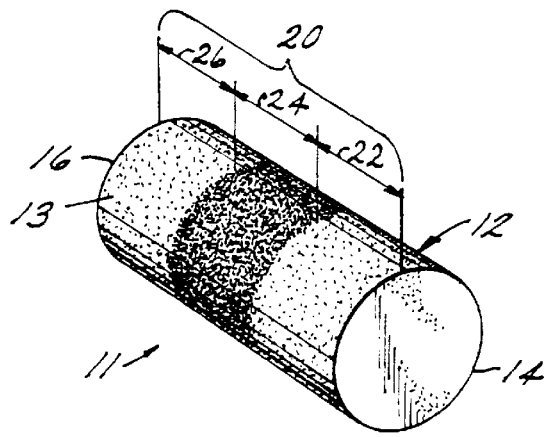
FIG. 2 is a perspective view of an earplug according to a second embodiment of the present invention.

Referring now to FIG. 2 in which an exemplary earplug construction according to a second embodiment of the present invention is illustrated and generally indicated at 11. The earplug 11 comprises a resilient polymeric foam body 12. The earplug 11 is similar to earplug 10 in that it is generally cylindrical in shape and includes the insertion end 14 and the opposing second end 16. In this second embodiment, the first, second, and third visual zones 22, 24, 26 comprise colored visual zones. As shown, the first, second, and third visual zones 22, 24, 26 each comprise a longitudinal color band. In the first embodiment, the visual zones 22, 24, 26 comprise continuous color bands each of which extends completely around the circumference of the earplug 11. In one exemplary embodiment, the first visual zone 22 has a red color, the second visual zone 24 has a yellow color, and the third visual zone 26 has a green color.

The first visual zone 22 comprises the insertion end 14 of the earplug 10. The second zone 24 comprises an intermediate portion of the earplug 11 and the third visual zone 26 comprises the second end 16 of the earplug 11. Accordingly, the first, second, and third visual zones 22, 24, 26 comprise visual zones which permit a safety officer or other individual to ascertain whether the wearer is complying with existing safety rules and regulations. For example, if the wearer inserts the earplug 11 into his/her ears and any amount of the red color of the first visual zone 22 is visually apparent to an observer, this indicates that a poor fit between the earplug 11 and the ear canal. Consequently, the earplug 11 should be removed and re-fitted. This also indicates that the wearer is only experiencing a low level of sound attenuation because the earplug 11 is not properly inserted into the ear.

If the earplug 11 is inserted so that the red color of the first visual zone 22 is not apparent but a portion of the yellow color of the second visual zone 24 is visually apparent, this indicates a moderate fit of the earplug 11. In other words, the wearer is obtaining some sound attenuation but is not obtaining maximum sound attenuation. If only a portion of the green color of the third visual zone 26 is visually apparent, then the fit between the earplug 11 and the ear canal is good and optimum attenuation is obtained. It being understood that the invention is not limited to the use of red, yellow, and green colors and a number of color combinations may be used so long as the colors mark or indicate a plurality of visual zones 20 which permit the observer to readily and easily know the type of fit between the earplug 11 and the ear canal and accordingly the level of sound attenuation being provided by earplug 11. Furthermore, the use of visual zones 22, 24, 26 are also used to aid the wearer in obtaining a better fit for the earplug 11. For example instead of the safety officer being the observer, the wearer may view the depth of insertion of the earplug 11 into the wearer's ear by using appropriate devices, e.g., a mirror. By observing which of visual zones 22, 24, 26 are visible, the wearer can immediately ascertain the degree of the fit and the corresponding level of sound attenuation being offered by the earplug 11. Adjustments may then be made, if needed, so that the earplug 11 is properly being worn.

Figure 4:
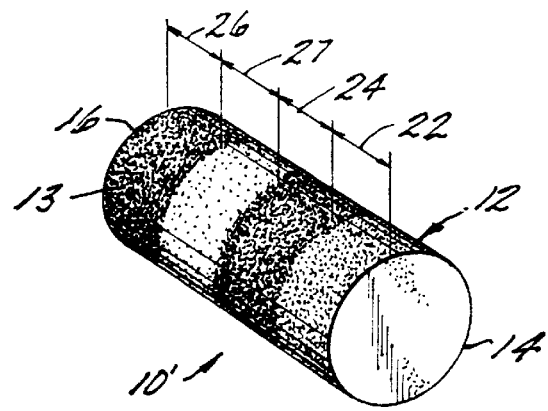
FIG. 4 is a perspective view of an earplug according to a fourth embodiment of the present invention.

Referring to FIG. 4, it being understood that the earplug 10' may have a greater number of visual zones 20 than the above-recited three visual zones 22, 24, 26. For example, the earplug 10' may have four or more visual color zones 22, 24, 26, 27 with each visual zone indicating the depth of insertion of the earplug 10' into the wearer's ear and likewise the level of sound attenuation which is provided by the earplug 10' as a result of the depth of insertion. As an example, the earplug 10' may have four or more visual zones 22, 24, 26, 27 where each layer of color that is inserted into the ear could indicate a different level of attenuation that could be achieved. Thus when the earplug 10' has, for example, four visual zones 22, 24, 26, 27, the wearer may be advised that in moderate noise environments the wearer needs to only insert the first two colored layers 22, 24 into the ear. In noisier environments, the wearer is advised to insert the first three colored layers 22, 24, 27 into the ear and for wearers in extremely noisy environments, the wearer is advised to insert all four colored layers 22, 24, 26, 27 into the ear.

Referring to FIGS. 1–6, the earplugs of the present invention may be formed from any number of suitable materials. For example, many of the externally and internally plasticized polymeric foams disclosed in commonly assigned U.S. Pat. No. Re. 29,487 are generally suitable for use as a material of construction for the present earplug. These plasticized polymeric foams are slow recovery foams which are not only comfortable, but also have been shown to deliver high-in-field noise protection at all frequencies. Other suitable materials are disclosed in commonly assigned U.S. Pat. No. 5,203,352 to Gardner which discloses temperature-dependent viscoelastic polymeric foam materials. Furthermore, commonly assigned U.S. Pat. No. 5,792,998 discloses a dynamically stiff foam material having a low static stiffness and a high dynamic stiffness which provides improved attenuation. For example, the foam component preferably has a dynamic spring constant of at least about 300 pounds per inch and a dynamic loss factor of at least about 0.25. One particularly suitable dynamically stiff foam material is a polyurethane material having the desired characteristics. Additional suitable polyurethane foam formulations are disclosed in U.S. Pat. No. 4,158,087 to Wood, which is hereby incorporated by reference in its entirety. Applicant hereby expressly incorporates in its entirety the contents of U.S. Pat. No. Re. 29,487; U.S. Pat. No. 5,203, 352; and U.S. Pat. No. 5,792,998.

Referring again to FIGS. 1–2. In one exemplary embodiment, the earplugs 10, 11 are formed of a suitable vinyl material. For purpose of illustration suitable manufacturing processes will be described with reference to the earplug 11 of FIG. 2. It being understood that the described manufacturing processes may be used to produce the other earplugs according to the present invention, e.g., earplug 10 of FIG. 1. For example, the vinyl materials disclosed in previously-mentioned U.S. Pat. No. Re. 29,487 are suitable for use in the present invention. The various individual color bands forming the first, second, and third visual zones 22, 24, 26 may be formed by casting the individually colored bands separately from one another and then curing the combined layers to form a foam sheet which is die cut (fabricated) into the earplug 11. For example, the first visual zone 22 is formed by casting a first vinyl foam portion having a first color. Next, the second visual zone 24 is formed by casting a second vinyl foam portion having a second color. The third visual zone 26 is formed by casting a third foam portion having a third color. All three vinyl foam portions are combined to form a composite which is then placed into an oven or the like and is cured to form the foam sheet fabricated into the earplug 11 having first, second, and third visual zones 22, 24, 26. By controlling the amount of laydown it is possible to obtain foam with reasonably controlled amounts of color layers. Thus, the earplug 11 is manufactured by a casting and curing process followed by fabrication to produce the plurality of visual color zones 22, 24, 26.

In another embodiment, the earplug 11 is formed of a suitable polyurethane material. Suitable polyurethane compositions are disclosed in previously-mentioned U.S. Pat. No. 5,792,998 and U.S. Pat. No. 5,203,352 and U.S. Pat. No. 4,158,087. Preferably, a predetermined number of different polyurethane colors are cast in succession, wherein the predetermined number equals the number of desired visual zones for the earplug 11. Another method of manufacturing comprises molding the earplug 11 with a predetermined number of colors, e.g., three. The method generally comprises molding the first color for the first visual zone 22, then the second color for the second visual zone 24, and finally the third color for the third visual zone 26. One of skill in the art will appreciate that the present invention is not limited to the above-recited manufacturing processes and other suitable processes may be used to manufacture the earplugs of the present invention.

In yet another manufacturing process, the first, second, and third visual zones 22, 24, 26 of the earplug 11 are formed using a post operation process in which the foam body 12 is manufactured having a base color and then the first, second, and third colors are added to at least an outer surface 13 of the foam body 12 to produce the first, second, and third visual zones 22, 24, 26, respectively. Any number of suitable techniques may be used to apply the first, second, and third colors to at least the outer surface 13. For example, the first, second, and third colors may be coated onto at least the outer surface 13 by any number of coating processes which permit the formation of distinct, demarcated visual zones 22, 24, 26. It being understood that the present invention is not limited to the processes recited herein.

Figure 3:
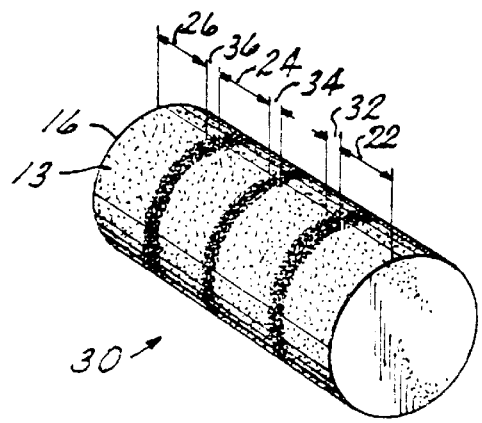
FIG. 3 is a perspective view of an earplug according to a third embodiment of the present invention.

Referring now to FIG. 3 in which an earplug according to a third embodiment is illustrated and generally indicated at 30. Earplug 30 is similar to earplug 11 except that the visual markings of the visual zones 22, 24, 26 are different. In this embodiment, the visual zones 22, 24, 26 are not continuous color bands but rather each of visual zones 22, 24, 26 comprises a visual zone having a corresponding visual marking line 32, 34, 36, respectively. Each of the visual marking lines 32, 34, 36 has a color which is distinctly different than the other colors of the visual marking lines 32, 34, 36. For example in the illustrated exemplary embodiment, the first visual marking line 32 has a red color, the second visual marking line 34 has a yellow color and the third visual marking line 36 has a green color. The width of each of first, second, and third visual marking lines 32, 34, 36 may be varied so long as the width is sufficient that the wearer or an observer may easily determine the depth of insertion by observing which of marking lines 32, 34, 36 are visible. In other words, for a low level of attenuation, the second and third marking lines 34, 36 are visible. For intermediate sound attenuation, the third marking line 36 is visible and for high level of sound attenuation, none of the first, second, and third marking lines 32, 34, 36 are visible.

Figure 5:
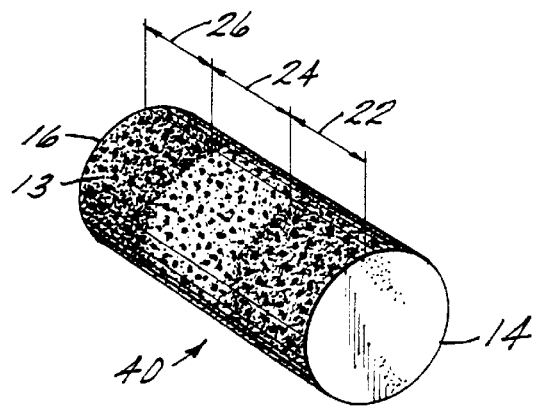
FIG. 5 is a perspective view of another embodiment of an earplug according to the present invention.

Referring now to FIG. 5 in which an earplug of a fifth embodiment of the present invention is illustrated and generally indicated at 40. Earplug 40 is similar to earplugs 11 and 30 except that the first visual zone 22 has a speckled design of a first color, the second visual zone 24 has a speckled design of a second color, and the third visual zone 26 has a speckled design of a third color. Preferably, each of the first, second, and third colors are distinct from one another so that the insertion depth of the earplug 40 is easily determined by viewing the earplug 40. In one exemplary embodiment, the first visual zone 22 has a red speckled design, the second visual zone 24 has a yellow speckled design, and the third visual zone 26 has a green speckled design.

Figure 6:
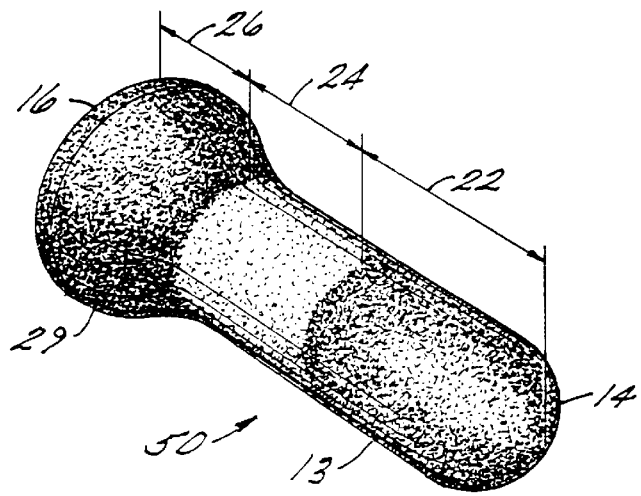
FIG. 6 is a perspective view of yet another embodiment of an earplug according to the present invention.

It being understood that the present invention is not limited to the color configurations or designs recited hereinbefore and any number of color schemes and designs may be used so long as at least the intermediate visual zone is visually distinct from remaining visual zones. In addition, the shape of the earplug according to the present invention is not limited to the shapes illustrated in the FIGURES. For example, FIG. 6 illustrates an earplug 50 according to another embodiment of the present invention where earplug 50 has a different shape. In this embodiment, the second end 16 has a greater diameter than the insertion end 14 and the third visual zone 26 has an outwardly flared surface 29.

Accordingly, the present invention provides an effective visual aid in determining whether the wearer is complying with existing safety rules, regulations, and the like and also provides a visual aid to permit the wearer to obtain a better fit between the earplug and the ear canal. By observing which visual zones of the earplug are inserted into the ear canal and which visual zones are visible as extending from the ear, an observer or the wearer himself/herself may easily determine the depth of insertion of the earplug into the ear canal. Advantageously, this permits the wearer to be easily instructed as to what depth of insertion is required in any given environment by simply referencing the visual zones of the earplug and indicating which visual zones may or may not be visible during use of the earplug. In addition, the multi-colored earplug of the present invention are visually pleasing and appealing.

It will be understood that a person skilled in the art may make modifications to the preferred embodiments shown herein within the scope and intent of the claims. While the present invention has been described as carried out in a specific embodiment thereof, it is not intended to be limited thereby but is intended to cover the invention broadly within the scope and spirit of the claims.

What is claimed is:

1. An earplug comprising:
a foam body having an insertion end, an opposing end, and an intermediate portion, the insertion end including a first visual zone, the opposing second end including a second visual zone, and the intermediate portion including a third visual zone, wherein at least the third visual zone has a color distinctly different from colors of the first and second visual zones.

2. The earplug according to claim 1, wherein the first and second visual zones have a yellow color and the third visual zone has a red color.

3. An earplug comprising:
a foam body having an insertion end, an opposing second end, and an intermediate portion, the insertion end including a first visual zone, the opposing second end including a second visual zone, and the intermediate portion including at least one intermediate visual zone, wherein the first, second, and intermediate visual zones indicate the relative depth of insertion of the foam body into an ear canal.

4. The earplug according to claim 3, wherein the at least one intermediate visual zone comprises a third visual zone and a fourth visual zone.

5. The earplug according to claim 3, wherein the first, second, and intermediate visual zones comprise continuous color bands.

6. The earplug according to claim 3, wherein the first visual zone comprises a continuous color band having a red color.

7. The earplug according to claim 3, wherein the second visual zone comprises a continuous color band having a green color.

8. The earplug according to claim 3, wherein the intermediate visual zone comprises a continuous color band having a yellow color.

9. The earplug according to claim 3, wherein the first, second, and intermediate visual zones each comprise a longitudinal color band, each of the longitudinal color bands having a color which is distinctly different from colors of the other longitudinal color bands.

10. The earplug according to claim 3, wherein the first visual zone has a first level of sound attenuation, the second visual zone having a second level of sound attenuation, and the intermediate zone having at least a third level of sound attenuation.

11. The earplug according to claim 10, wherein the first level of sound attenuation is less than the third level which is less than the second level.

12. The earplug according to claim 3, wherein the foam body is formed of a material selected from the group consisting of polyurethane, acrylic, acrylic blends, polyvinyl chloride or mixtures thereof.

13. The earplug according to claim 3, wherein the first visual zone defined by a first marking line, the second visual zone being defined by a second marking line, the intermediate visual zone being defined by a third marking line.

14. The earplug according to claim 13, wherein at least the second marking line has a color distinctly different from colors of the first and third marking lines.

15. The earplug according to claim 3, wherein the first visual zone comprises a speckled design of a first color, the second visual zone being a speckled design of a second color, the intermediate visual zone being a speckled design of a third color.

16. A multi-color earplug having visual indicia for indicating a level of compliance and a level of sound attenuation, the earplug comprising:
- a foam body having an insertion end, an opposing second end, and an intermediate portion therebetween;
- a first visual indicia formed at the insertion end for indicating a first position of the earplug in an ear;
- at least one second visual indicia formed at the intermediate portion for indicating a second position of the earplug in the ear; and
- a third visual indicia formed at the second end for indicating a third position of the earplug in the ear.

17. The earplug according to claim 16, wherein the first, at least one second, and third visual indicia each comprise a continuous color bands.

18. The earplug according to claim 16, further including:
- a fourth visual indicia formed at the intermediate portion.

19. The earplug according to claim 16, wherein the insertion of only the first visual indicia into the ear indicates a low level of sound attenuation, the insertion of the first and at least one second visual indicia into the ear indicating a moderate level of sound attenuation, and insertion of the first, at least one second, and third visual indicia into the ear indicating a full level of sound attenuation.

20. The earplug according to claim 16, wherein at least the second visual indicia is distinctly different from the first and third visual indicia.

* * * * *

UNITED STATES PATENT AND TRADEMARK OFFICE
CERTIFICATE OF CORRECTION

| | |
|---|---|
| PATENT NO. | : 6,105,715 |
| DATED | : August 22, 2000 |
| INVENTOR(S) | : Richard E. Knauer |

It is certified that error appears in the above-identified patent and that said Letters Patent is hereby corrected as shown below:

<u>Column 10,</u>
Line 3, after "color" delete "bands" and insert therefor -- band --

Signed and Sealed this

Seventeenth Day of August, 2004

JON W. DUDAS
*Acting Director of the United States Patent and Trademark Office*